United States Patent [19]

Lindmo et al.

[11] 4,408,877

[45] Oct. 11, 1983

[54] DEVICE FOR HYDRODYNAMIC FOCUSSING OF A PARTICLE-SUSPENSION IN A LIQUID FLOW CYTOPHOTOMETER

[75] Inventors: Tore Lindmo, Sofiemyr; Harald B. Steen, Oslo, both of Norway

[73] Assignee: Ernst Leitz Wetzlar GmbH, Wetzlar, Fed. Rep. of Germany

[21] Appl. No.: 220,038

[22] PCT Filed: Apr. 10, 1980

[86] PCT No.: PCT/EP80/00021

§ 371 Date: Dec. 10, 1980

§ 102(e) Date: Dec. 8, 1980

[87] PCT Pub. No.: WO80/02198

PCT Pub. Date: Oct. 16, 1980

[30] Foreign Application Priority Data

Apr. 10, 1979 [NO] Norway ............................. 791228

[51] Int. Cl.³ ............................................ G01N 33/48
[52] U.S. Cl. ......................................... 356/38; 356/39
[58] Field of Search ................. 356/38, 39, 335, 336, 356/440, 441, 442, 246; 250/222 PC, 222.2; 350/81, 90, 534

[56] References Cited

U.S. PATENT DOCUMENTS 3,661,460  5/1972  Elking et al. ....................... 356/442
4,338,024  7/1982  Bolz et al. ............................ 356/39

FOREIGN PATENT DOCUMENTS 7333009  9/1973  Fed. Rep. of Germany ...... 356/246
2640974  3/1978  Fed. Rep. of Germany ........ 350/81
2709399  9/1978  Fed. Rep. of Germany .

Primary Examiner—Vincent P. McGraw
Attorney, Agent, or Firm—Schwartz, Jeffery, Schwaab, Mack, Blumenthal & Koch

[57] ABSTRACT

Device for liquid flow cytophotometer including a device for hydrodynamic focussing (4,6) of a cell- or particle-suspension towards a measuring area, and an optical excitation-and detection-system (9), preferentially based on oil immersion optics, characterized by the focussing device being formed at or in relation to the system's optical axis-rotating nozzle assembly (1) directed towards a surface (7) which is open in relation to the surrounding atmosphere and situated on the optics (9), forming the optics' measuring area, thus supplying a laminar liquid flow of the above-mentioned suspension.

10 Claims, 1 Drawing Figure

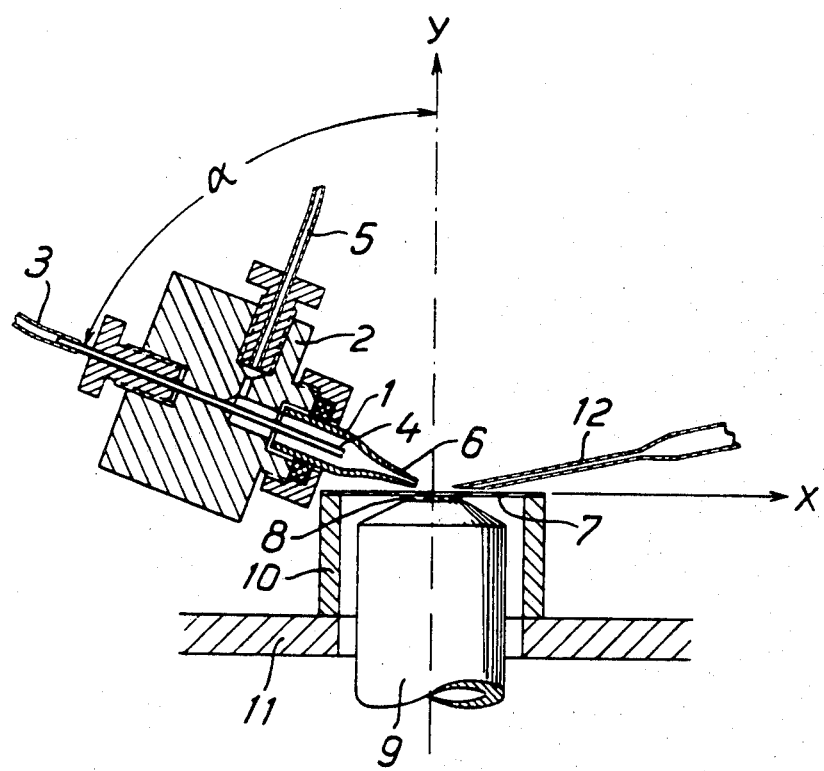

DEVICE FOR HYDRODYNAMIC FOCUSSING OF A PARTICLE-SUSPENSION IN A LIQUID FLOW CYTOPHOTOMETER

BACKGROUND OF THE INVENTION

The present investigation concerns a device representing a new kind of liquid flow system in connection with liquid flow cytophotometers.

Cytophotometry is an important operating method in cell biology research, especially in the field of comprehensive cancer research. Thus, it is considered important to investigate the abnormal growth in cell populations where new cells are created by means of cell division. During its synthesis phase the cell will double its DNA-content. In this way one gets two new cells when the cell divides (the mitotic phase). By measuring the DNA-content per cell it is possible to determine the distribution of the cells on the various cell cycle phases. The fraction of cells containing an increased DNA-content in a cell population can be a measure of the multiplying activity. It is important that the distribution of the cells in a cell population on the various cell cycle phases can be determined with a great accuracy. Statistical errors can only be avoided by measuring several thousand cells. This necessitates that the individual measurements are done very rapidly.

The so-called liquid flow cytophotometry is a technique which is now applied for such measurements. Today there is an increasing use of this technique in connection with research as well as diagnostic purposes. The principle of such a method is to lead a limited flow of cells stained with a fluorescent dye, quantitatively bound to the cell components which are to be studied, through a beam of exciting light and then measure the intensity of the resulting fluorescence pulses. The distribution of the cells with regard to a certain component, such as DNA, can thus be determined with great accuracy and with a rate of the order of $10^3$ per second. The cells are automatically transported to the measuring spot in a liquid flow, usually water.

Thus, the cells are not spread on a glass plate, but are kept in a liquid suspension. This suspension is driven through a capillary tube, and by means of a concentric sheath flow flowing around the tube mentioned above and in the same direction as the cells and containing no particles, the cell flow is hydrodynamically focussed so that the cells pass by through a strictly limited area in the cytophotometer's measuring focus. The cells pass by one after another through this measuring area at a high speed, just like mentioned above.

The measuring of the cell components is done by means of a microfluorometer. As mentioned above, the cell component must be stained with a fluorescent dye. When a cell containing such a fluorescent dye passes through the microscope lens' focussing area, it excites fluorescent light which is accumulated by the lens and then lead to a photomultiplier. The signal from this photomultiplier is registered and expresses the cell's contents of the component in question.

A well-known liquid flow cytophotometer applies the technique mentioned above. It comprises a closed system including a sheath flow measuring chamber. This chamber consists of a glass- or metal body with channels in a T-form. By means of suction the sheath flow and the particle suspension which is to be measured are led through the channel forming the T-form's system, and accurately centered along the system's optical axis. In this way one gets a measuring area at the T-form's peak, i.e. at the area of the perpendicular channels constituting the T-form's arms. One of these perpendicular channels transports a cleansing agent, while the other represents a drainage channel for the fluid flow containing measured particles. Thus, by using this well-known technique one gets a supply of particles along the optical axis with a focussing of every particle through the optical focus lying on the measuring aperture level. The optical system which is applied here comprises a so-called oil immersion optics which is known to the expert. The optics is in contact with the liquid suspension containing the particles or the cells which are to be studied.

There are liquid flow cytophotometers using closed sheath flow measuring chambers, but where the liquid flow is led perpendicularly through the exciting light in the measuring area.

Further, there are liquid flow cytophotometers where a focussed liquid jet containing particles which are to be studied, is led—in the air—through an excitation light falling on the liquid jet. This light is focussed in the liquid jet, so that when single particles, which can be stained with a fluorescent dye, pass through this light focus, one will have a pulse of fluorescent light which is picked up by a photo cell.

SUMMARY OF THE INVENTION

The well-known liquid flow cytophotometers mentioned above are complicated, and that leads to high construction expenses. Nowadays there is an ever increasing demand for a simple and inexpensive instrument which can be used in connection with routine investigations. The present invention provides a construction using a standard fluorescence microscope—preferentially with immersion optics—with a suitable photometer, and hydro-dynamic focussing of a particle suspension. This construction is relatively inexpensive, easy to operate and gives a high resolution and stability.

Thus, the present investigation provides a device in connection with liquid flow cytophotometers comprising a device for hydrodynamic focussing of a cell- or particle-suspension towards a measuring area, and also an optical excitation- and detection-system, preferentially based on oil immersion optics. This device is characterized by the focussing device's design; the device is formed as a—in relation to the system's optical axis—rotating nozzle assembly aiming at a—in relation to the surrounding atmosphere—free surface situated on the optics, which constitutes the optics' measuring area. In this way one obtains a laminar liquid flow of the suspension mentioned above.

The term "—in relation to the surrounding atmosphere—free surface" means that this device does not apply a closed chamber, as mentioned above, wherein the particle suspension is led and focussed, but that one lets the liquid jet pass by towards the measuring area in the air. Thus, the nozzle should preferentially be in the surrounding free atmosphere. Using this invention the measuring area can be the surface of a transparent plate, for instance a replaceable cover glass, in contact with the optics.

The present device provides measuring results at least as good as the best results obtained with the above mentioned constructions. Further, the present device results in a much easier setting up and focussing of the instrument than is the case with well-known systems.

Due to the measuring area and the nozzle being situated in the air, it is easier to inspect and clean the instrument. Thus, the cover glass in the measuring area can easily be washed or replaced. Further, it is easy to flush the hydrodynamic focussing device including the nozzle. As the nozzle assembly is revolving in relation to the system's optical axis, various angles of incidence can be obtained for the liquid jet containing particles. Thus, the nozzle assembly can be turned between a vertical and a horizontal position in relation to the level of the measuring area. The nozzle assembly's rotating device makes it possible to measure the asymetric effects of the particles or the cells which are being studied. This is of interest when one needs information about the particles' form. Such effects are difficult to measure when the liquid jet is permanently vertically aimed at the measuring area's level, as with the above mentioned well-known systems where a closed liquid flow chamber is applied.

A drainage device is situated in the periphery of the optics' measuring area, and this device is preferentially constituted by a tube with suction.

BRIEF DESCRIPTION OF THE DRAWING

In the following the invention will be described with reference to the enclosed FIGURE showing a schematic side view of the present device. The nozzle assembly is adjusted so that it forms an acute angle with the level of the measuring area.

DETAILED DESCRIPTION OF PREFERRED EMBODIMENTS

The nozzle assembly (1) is placed in a holder (2) with an inlet tube (3) for the sample suspension containing particles which are to be studied. This inlet tube (3) is connected to a thin tube which extends centrally and axially into the nozzle assembly (1). Further, the holder (2) has an inlet tube (5) for sheath flow liquid, and this tube leads into the nozzle assembly (1) so that the sheath flow liquid is able to flow around the cavity needle (4). The nozzle assembly has a nozzle (6) with its outlet over a cover glass (7) situated above and in contact with an immersion oil coating (8) on a microscope objective (9).

The FIGURE shows that the cover glass (7) is resting on a holder (10) connected to the microscope stage. As mentioned above, the nozzle assembly (1) can be rotated in relation to the system's optical axis, i.e. between a vertical and a horizontal position, represented by the y-axis and the x-axis, respectively. In the FIGURE the holder (2) with the nozzle assembly (1) and the nozzle (6) are rotated in relation to the y-axis with an acute angle called α. In order to remove liquid from the cover glass (7) as this flows out of the nozzle (6) a drainage (12) connected to a suction pipe has been set up.

As for a further description of the liquid flow cytophotometer, describing how the present and schematically shown device is operated, literature in this field which is known to the specialist is referred to and incorporated by reference.

When using the present device in a liquid flow cytophotometer, a particle- or cell-suspension is lead through the tube (3). At the same time a sheath flow liquid is lead through the tube (5), and by means of the nozzle (6) on the nozzle assembly (1) these two components create a hydrodynamically focussed sample stream consisting of a liquid flow in the air, which is directed towards the microscope cover glass (7) on the objective system (8, 9). In this way a laminar, well-defined and stable flowing area is obtained on the cover glass (7). This can be observed through the fluorescence microscope in incident light, i.e. with the excitation light focussed through the objective (9). The liquid is removed from the cover glass (7) by means of the drainage (12).

It has been found that large angles of incidence, for instance α=70°, give somewhat better results than those obtained when using other settings of the angle of incidence, for instance α=0°, i.e. the liquid flow is led perpendicularly onto the cover glass (7).

Generally, the present device may be applied in connection with any fluorescence microscope with the illumination through the objective. The high speed of the liquid flow in the air (approximately 10 m/sec.) and the laminar flowing pattern on the cover glass has the effect that the system may be orientated in any direction. The present device enables the specialist to set up a liquid flow cytophotometer which is superior as regards resolution, simplicity and rational use, and which makes it possible to obtain measuring results at least as good as those obtained by well-known commercially available systems.

When set up vertically the present device may be applied for volume measurements based on the Coulter principle by applying a metal coating on the inner surface of the nozzle (6) and as a ring on the upper surface of the cover glass (7), thus providing electrodes for the ionic current applied for such measurements. In this way the short liquid flow between the nozzle (6) and the cover glass (7) will constitute the sensing region of a change in the electrice impedance induced by a passing particle or cell. Furthermore, light scatter measurements may be made by using a phase contrast objective and an annular detector situated in the shade thrown by the phase contrast ring. Large angles of incidence (i.e. 70° C. or more) are most practical for such light scatter measurements, because such angles of incidence make it possible to center a light scatter detector in the area of the optical axis.

We claim:

1. A device for carrying out liquid flow cytophotometry, comprising:
    an optical excitation and detection system having an optical axis and an object plane;
    a plate having a surface which is positioned in the object plane of said optical system to define a measuring area and which is open in relation to the surrounding atmosphere; and
    means for hydrodynamically focussing a suspension of cells or particles and for openly directing the suspension through the surrounding atmosphere toward and against said measuring area defined by the surface of said plate to produce a laminar flow of the suspension on said surface, said suspension being focussed into a stream wherein the cells or particles pass by one after another through the measurement area.

2. A device according to claim 1, wherein said focussing and directing means comprises a separate nozzle assembly.

3. A device according to claim 2, wherein said nozzle assembly comprises a central capillary tube for the suspension and a coaxially surrounding nozzle for a sheathing liquid.

4. A device according to claim 2, further comprising means for rotating said nozzle assembly in relation to said optical axis between a first position parallel to said optical axis and a second position essentially perpendicular to said optical axis.

5. A device according to claim 1, wherein said plate comprises a transparent plate in contact with said optical system.

6. A device according to claim 1, further comprising means, including a suction tube situated at the periphery of said measuring area, for draining the suspension from the measuring area.

7. A device according to claim 1, wherein the surface of said plate is essentially horizontal and said focussing and directing means is positioned so as to direct said stream at an acute angle with respect to the vertical.

8. A device according to claim 1, wherein said focussing and directing means is positioned so as to direct said stream at an acute angle with respect to said optical axis.

9. A device according to claim 8, wherein said angle is greater than about 70°.

10. A device according to claim 1, wherein said device comprises means for readily interchanging said plate.

* * * * *